United States Patent
Aravena et al.

(10) Patent No.: US 7,300,283 B2
(45) Date of Patent: *Nov. 27, 2007

(54) ABUTMENT SCREW WITH SPRING-WASHER

(75) Inventors: Ines Aravena, Camarillo, CA (US); Ajay Kumar, Palmdale, CA (US)

(73) Assignee: Zimmer Dental Inc., Carlsbad, CA (US)

(*) Notice: Subject to any disclaimer, the term of this patent is extended or adjusted under 35 U.S.C. 154(b) by 199 days.

This patent is subject to a terminal disclaimer.

(21) Appl. No.: 11/194,254

(22) Filed: Aug. 1, 2005

(65) Prior Publication Data

US 2005/0266383 A1    Dec. 1, 2005

Related U.S. Application Data

(63) Continuation of application No. 10/302,070, filed on Nov. 22, 2002, now Pat. No. 6,932,606.

(60) Provisional application No. 60/385,814, filed on Jun. 4, 2002.

(51) Int. Cl.
A61C 8/00        (2006.01)

(52) U.S. Cl. ..................................... 433/173

(58) Field of Classification Search ............ 433/173, 433/174, 175, 172, 177

See application file for complete search history.

(56) References Cited

U.S. PATENT DOCUMENTS

| | | | |
|---|---|---|---|
| 4,462,730 A * | 7/1984 | Knohl | 411/371.1 |
| 5,695,335 A | 12/1997 | Haas et al. | |
| 5,711,669 A | 1/1998 | Hurson | |
| 5,733,122 A | 3/1998 | Gordon | |
| 6,168,436 B1 * | 1/2001 | O'Brien | 433/173 |
| 6,447,295 B1 | 9/2002 | Kumar et al. | |
| 6,932,606 B2 * | 8/2005 | Aravena et al. | 433/173 |

* cited by examiner

*Primary Examiner*—Melba Bumgarner
(74) *Attorney, Agent, or Firm*—Fitch, Even, Tabin & Flannery

(57) ABSTRACT

A dental retaining screw used to secure dental components, such as abutments, copings, and prosthesis to dental implants. The screw has a body formed from titanium and a spring-washer formed from gold. The spring-washer is adapted to prevent the screw from loosening or losing preload once tightened to the implant. The spring-washer includes an annular body with a plurality of flexible legs extending from the annular body; the legs prevent the screw from coming loose during shipping or while attached to an abutment.

13 Claims, 7 Drawing Sheets

ABUTMENT SCREW WITH SPRING-WASHER

CROSS-REFERENCE TO RELATED APPLICATIONS

The present application is a continuation application of U.S. application Ser. No. 10/302,070, filed Nov. 22, 2002 now U.S. Pat. No. 6,932,606 and entitled Abutment Screw With Spring-Washer, which claims the benefit under 35 U.S.C. 119(e) of U.S. Provisional Application Ser. No. 60/385,814, filed Jun. 4, 2002 and entitled Abutment Screw With Spring-Washer, both of these applications being hereby incorporated herein by reference.

FIELD OF THE INVENTION

The present invention relates generally to the field of dental implantology and, more specifically, to retaining screws used to secure dental components, such as abutments, copings, and prosthesis to dental implants.

BACKGROUND OF THE INVENTION

Retaining screws in the field of dental implantology or dental prosthetics are very important since they are used to fasten and hold together various dental components. These retaining screws, for example, fasten the dental abutment to the dental implant. Unfortunately, prior dental retaining screws tend to loosen over time. The loosening of these screws has caused many problems, and much effort has been devoted to solving these problems.

Dental retaining screws are typically fabricated from titanium. On one hand, titanium is ideal for this indication since it is strong, light-weight, and biocompatible. On the other hand though, titanium has a high coefficient of friction that makes it very susceptible to loosening over time. Specifically, a large percentage of the torque applied to a dental retaining screw is lost to overcoming the high frictional contact between the screw threads and threaded bore of the implant and between the screw head and seating surface of the abutment. According to some estimates, approximately 50% of the applied torque is lost in overcoming the mating friction under the screw head; and 40% of the applied torque is lost in the threads. As such, only about 10% of the applied torque exerted on the screw head is actually exerted as preload or tensile force stretching and tightening the screw.

Retaining screws tend to loosen in dental applications also because these screws are exposed to large loads and extended vibrations. Occlusal forces from chewing, talking, grinding, brushing, etc. continuously load the prosthetic tooth and accompanying retaining screw. These forces, over time, can decrease the preload and loosen the screw. Once the screw loosens, the joint between the prosthetic components can open or form gaps. The dental components, such as the prosthesis, the abutment, and the screw, can then bend or even break.

Over the years, many solutions have been proposed to reduce the occurrence of titanium screws loosening in dental applications. One solution is to increase the applied torque to the screw. This solution has limitations since the retaining screws can be tighten or loaded above the yield point of the material. In this instance, the screw can be permanently damaged and elastically unable to return to its original shape and position. Further yet, the maximum, attainable preload can be lessened if the screw is permanently damaged and deformed.

Many other solutions have been devoted to reducing the coefficient of friction either between the screw head and the mating surface of the dental component or between the screw threads and threaded bore of the implant. In some instances, screws have been made of gold-alloy material to reduce the co-efficient of friction, but their soft material causes deformation of their threads upon tightening.

In other instances, surface coatings have been placed on the retaining screw to reduce the coefficient of friction. U.S. Pat. No. 6,447,295, entitled "Diamond-Like Carbon Coated Dental Retaining Screws" and incorporated by reference herein, teaches a retaining screw coated with diamond-like carbon. Further, U.S. Pat. No. 5,711,669, entitled "High Load Factor Titanium Dental Implant Screw" teaches a retaining screw coated with a soft, deformable, biocompatible material that is malleable and subject to cold flow.

These coatings reduce the coefficient of friction of the retaining screw, but the coatings have disadvantages. First, the coatings can be expensive. Additionally, they can wear over time or become removed or scraped during tightening. Further, although they can reduce the coefficient of friction, they do not prevent or inhibit the retaining screw from loosening or losing preload due to occlusal forces, vibrations during masticulation, and the like.

It would be advantageous to have a dental retaining screw that could be used to secure prosthetic components to a dental implant yet not be prone to loosen or lose preload.

BRIEF SUMMARY OF THE INVENTION

The present invention is directed toward dental retaining screws used to secure dental components, such as abutments, copings, analogs, cuffs, healing members, and prosthesis to dental implants. The retaining screw has a proximal end with a head portion having a locking mechanism. This locking mechanism includes a spring-washer with an annular body and a plurality of resilient legs projecting downwardly from the body. Each leg has a distal end with a locking component shaped as a foot or projection extending outwardly from the leg.

The spring-washer is adapted to threadably engage the exterior threads on the retaining screw. The spring-washer can removably connect to the body of the screw with any one of various connections, such as a press-fit or snap-fit. In this regard, the outer surface of the retaining screw includes a housing adapted to receive the legs of the spring-washer. The housing is configured as a plurality of channels or grooves, wherein each channel receives one leg of the spring-washer. Once the spring-washer is connected to the body of the screw, the legs are adapted to flexibly move in an axial direction in the channels.

The dental component includes an internal cavity with a locking mechanism along the interior surface of the cavity. Preferably, this locking mechanism is configured as a plurality of elongated channels that extend parallel to the longitudinal axis of the dental component. Preferably, the channels are formed along the interior surface and are equally spaced apart.

The retaining screw fits inside the interior cavity of the dental component and abuts a ledge to connect the dental component and implant. When the retaining screw is in place and appropriate torque and preload have been applied to it, the screw will not loosen while threadably connected to the implant. In this regard, the locking mechanism of the retaining screw and the locking mechanism of the dental component engage to prevent counterclockwise rotational movement of the retaining screw. Specifically, the legs of the spring-washer bias the locking component out of the housing and into the locking mechanism of the dental component. The projections or feet, thus, engage or lock with the channels along the interior surface of the dental component. As such, the retaining screw is prevented from rotating or losing preload while tightened and connected to the implant.

One important advantage of the present invention is that once the retaining screw is tightened to a selected torque level, the locking mechanisms of the dental component and retaining screw prevent or reduce the possibility that the retaining screw will loosen. The retaining screw will not tend to loosen even when exposed to large loads and extended vibrations, such as occlusal forces from chewing, clinching, grinding, talking, brushing, etc. Hence the stability of the dental implant system is improved and a secure and reliable fastening mechanism or coupling is provided between the dental component and the dental implant.

As another advantage, since the retaining screw is much less likely to loosen, then the joint between the prosthetic components is much less likely to form an opening or gap as a result of a loose retaining screw. Further, the dental components, such as the prosthesis, the abutment, and the screw, are not as likely to bend or even break.

As another important advantage of the present invention, the spring-washer body of the retaining screw is formed from titanium, and the spring-washer is formed from gold. The gold spring-washer advantageously provides a reduced coefficient of friction between the contacting surface of the retaining screw and the seating surface of the dental component, such as the abutment. As such, the screw is capable of obtaining a higher preload or clamping force between the dental component and implant. Further more, the coefficient of friction between gold and titanium is 60% less than titanium to titanium. This reduction in friction results in a higher preload. The spring washer can be made out of titanium and can be later anodized and or diamond coating can be applied to the surface to achieve the same affect as gold.

As a further advantage, the locking mechanisms of both the dental component and retaining screw are biocompatible and resistive to corrosion. The retaining screw is also relatively inexpensive to manufacture.

Another advantage is that the spring-washer ensures that the screw is retained in the abutment during shipping and placement of the abutment in the mouth without the need of internal threads inside the abutment. As such, the screw will not fall out from the abutment.

Accordingly, the present invention comprises a combination of features and advantages that overcome various problems, deficiencies, or shortcomings associated with prior devices. The various features and advantages of the invention will be readily apparent to those skilled in the art upon referring to the accompanying drawings and reading the following detailed description of the preferred embodiments of the invention.

BRIEF DESCRIPTION OF THE DRAWINGS

For a more detailed description of preferred embodiments of the present invention, reference will now be made to the accompanying drawings, wherein.

DETAILED DESCRIPTION OF PREFERRED EMBODIMENTS

Figure 1:
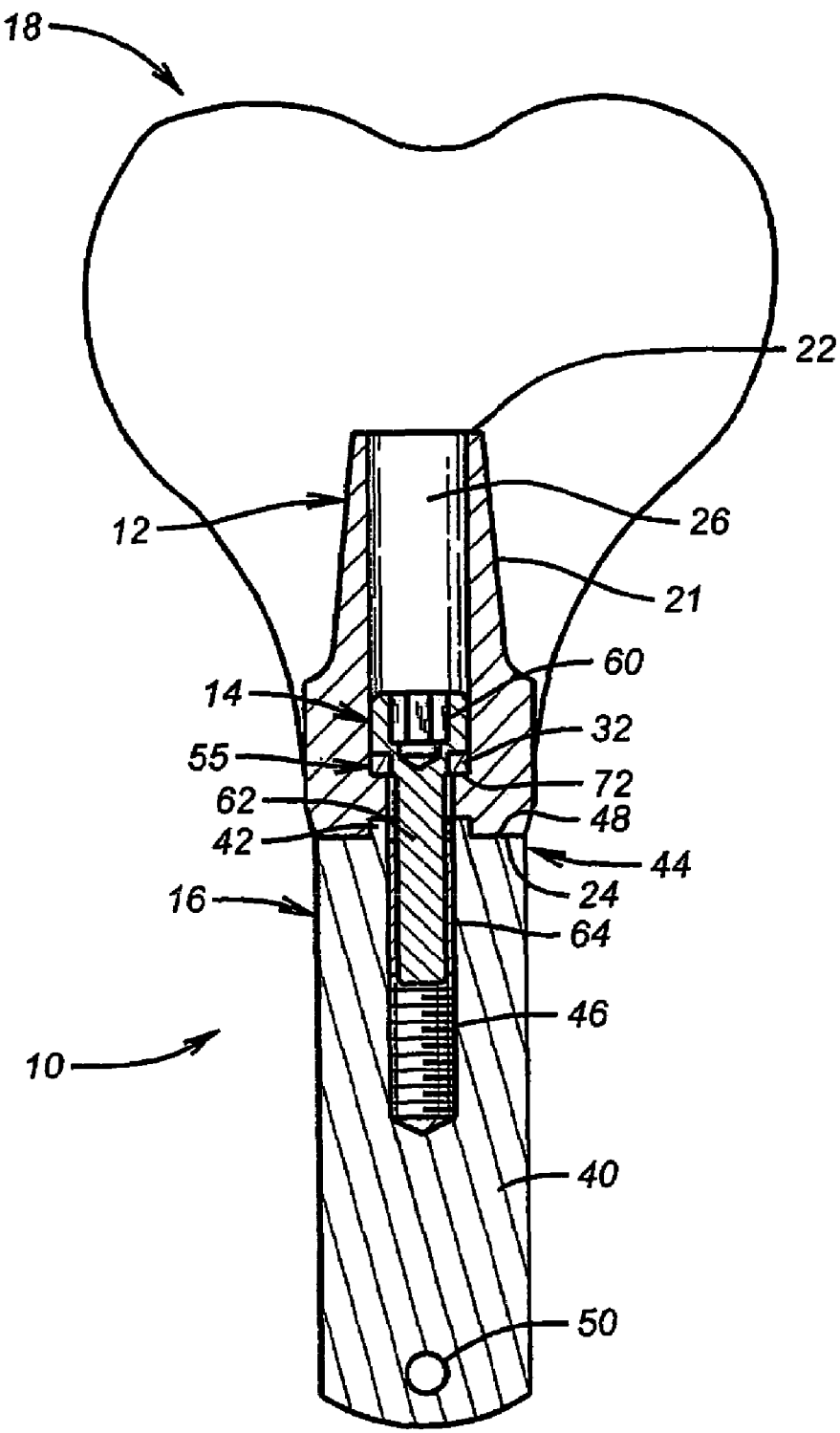
FIG. 1 is a partial cross-sectional view of a dental implant system supporting a prosthetic tooth and having a retaining screw in accordance with a preferred embodiment of the invention.

FIG. 1 illustrates a dental prosthetic implant system 10 having features in accordance with one preferred embodiment of the present invention. The dental implant system 10 generally comprises a dental component 12 (shown as an abutment), a retaining screw or bolt 14 (shown as an abutment retaining screw), and a dental implant, fixture, or root 16. The dental implant 16 is adapted to be received in a hole, osteotomy, or alveolar cavity in a jawbone of a patient. The retaining screw 14 serves the purpose of fastening and holding the abutment 12 to the implant 16.

The dental component 12 and retaining screw 14 can be commercialized as a dental kit. This dental kit may further include additional dental components known to those skilled in the art. Such dental components include dental copings, analogs, healing collars, healing abutments, cuffs, prosthesis, and the like.

In one preferred embodiment, the dental implant system 10 further comprises a dental restoration, prosthesis, or artificial tooth 18. The abutment 12 supports the restoration 18 in the mouth of a patient. The restoration 18 can be cemented to the abutment 12. Alternatively, or in addition, a separate screw (not shown) can be used to mount and retain the prosthesis 18 on the abutment 12.

Figure 2:
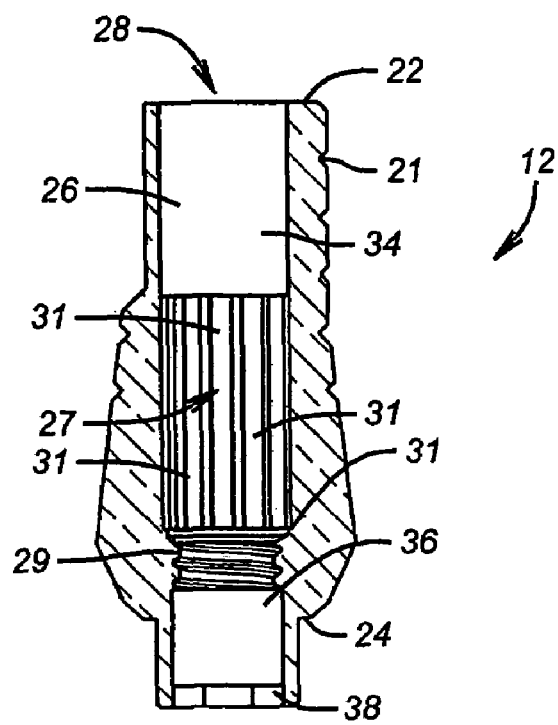
FIG. 2 is a cross-sectional view of one embodiment of an abutment according to the invention.
Figure 3:
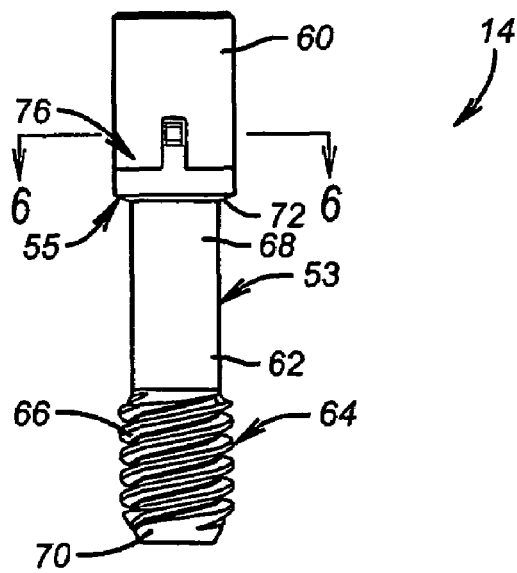
FIG. 3 is a side view of a retaining screw according to the invention.

As shown in FIGS. 1 and 2, the abutment 12 is generally elongated in shape and can have a variety of shaped exterior surfaces 21 adapted to seat and retain the prosthesis 18. For example, the abutment exterior surface 21 can be tapered, conical, cylindrical, straight, angled, contoured, or combinations thereof.

As the skilled artisan will recognize, the present invention can be embodied utilizing a wide variety of commercially available abutments. Thus, the abutment 12 can comprise, for example, the UCLA abutment or abutments sold by Centerpulse Dental Inc. of Carslbad, Calif.

The abutment 12 has a top end 22, a bottom seating end/surface 24 for interfacing or abutting with the implant 18, and an internal, through cavity or bore 26. This cavity has a generally circular opening 28 at the top end 22 and is adapted to receive the retaining screw 14. The cavity 26 further includes an internal seating surface, shoulder, seat, or ledge 32 that serves as a seating surface for the head of the screw 14. Preferably, the shoulder 32 is generally flat, annular or ring-like in shape, but other embodiments are known to those skilled in the art.

The shoulder or abutting surface 32 divides or partitions the through cavity 26 into an upper generally cylindrical cavity, portion, or surface 34 and a lower (or middle) generally cylindrical cavity, portion, or surface 36. The cavity 34 and cavity 36 are in communication with one another with the cavity 34 having a diameter larger than that of the cavity 36.

The cavity 36 is further in communication with a generally hexagonal socket, portion, or surface 38 at the bottom end 24 of the abutment 12. The hexagonal socket 38 permits anit-rotational mating, coupling, or attachment between the abutment 12 and implant 16.

As shown in FIG. 2, cavity 26 includes a locking mechanism 27 formed along the interior surface of the bore. Preferably, the locking mechanism is formed above a threaded section 29. This locking mechanism includes a plurality of locking members 31. In this embodiment, these locking members are formed as elongated channels or grooves that extend in a longitudinal or axial direction in the interior surface of the cavity 26. Preferably, the locking members are spaced about 6° to 18° apart.

Turning back to FIG. 1, the implant 16 can be any one of a wide variety of dental implants, for example, a threaded implant, a cylindrical implant, or a tapered implant, as are known in the art, such as a tapered or straight Screw-Vent implant of Centerpulse Dental Inc. The implant 16 comprises a body or root portion 40 adapted to engage an osteotomy or alveolar cavity in the jawbone of a patient. The implant includes a hexagonal post or protrusion 42 at a top end 44. A blind internal threaded socket or bore 46 originates from the top end 44 and into the implant body portion 40. The threaded socket 46 is adapted to threadably engage the abutment retaining screw 14. A seating surface 48 generally circumscribes the hexagonal post 42 to engage, contact, or abut against the opposing abutment seating surface 24. The implant body portion 40 may include a passage 50 formed to permit in-growth of bone and tissue for locking or anchoring the implant 16 in the osteotomy.

The hexagonal post 42 of the implant is configured to provide anti-rotational engagement with the abutment hexagonal socket 38 (FIG. 2). Alternatively, a mating post may be provided at the bottom end of the abutment 12 to interlock with a corresponding mating socket at the top end of the implant 16.

Turning now to FIGS. 3-7, the abutment retaining screw 14 is generally dimensioned and configured to adapt to a particular implant-abutment pair. The retaining screw 14 generally comprises an elongated body 53 and a spring-washer 55. The body further includes an upper head or cap portion 60 in mechanical communication with a shank portion 62 that extends downwardly therefrom. The shank 62 comprises a threaded portion 64 having external threads 66 adapted to threadably engage the threaded socket 46 of the implant 16 (FIG. 1). The threaded portion 64 is in mechanical communication with an upper non-threaded portion 68 and a lower non-threaded portion 70 at the distal tip of the shank 62.

The screw head 60 is preferably generally cylindrical in shape and includes a lower contacting, seating, or abutting surface 72 at the bottom of the spring-washer 55 for engaging the opposed seating surface, or shoulder 32 of the abutment 14 (FIG. 2). Preferably, the contacting surface 72 is generally annular or ring-like in shape to generally conform to the shape of the abutment shoulder 32 (FIG. 2). Additionally, the screw head 60 preferably has a generally hexagonal cavity or socket 74 for receiving a torque wrench or other suitable tool.

The retaining screw 14 includes a locking mechanism 76 adapted to prevent the screw from loosening while tightened to the implant. The locking mechanism generally includes the spring-washer 55 and corresponding housing 78. The housing is formed along the external surface of the body 53 on the head 60. Preferably, the housing is formed as a plurality of elongated channels, slots, or grooves 80. These channels extend from the distal end of the head 60 toward the proximal end where the socket 74 is located. As shown best in FIGS. 6 and 7, the channels 80 have a rectangular or square shape in cross section.

Figure 4:
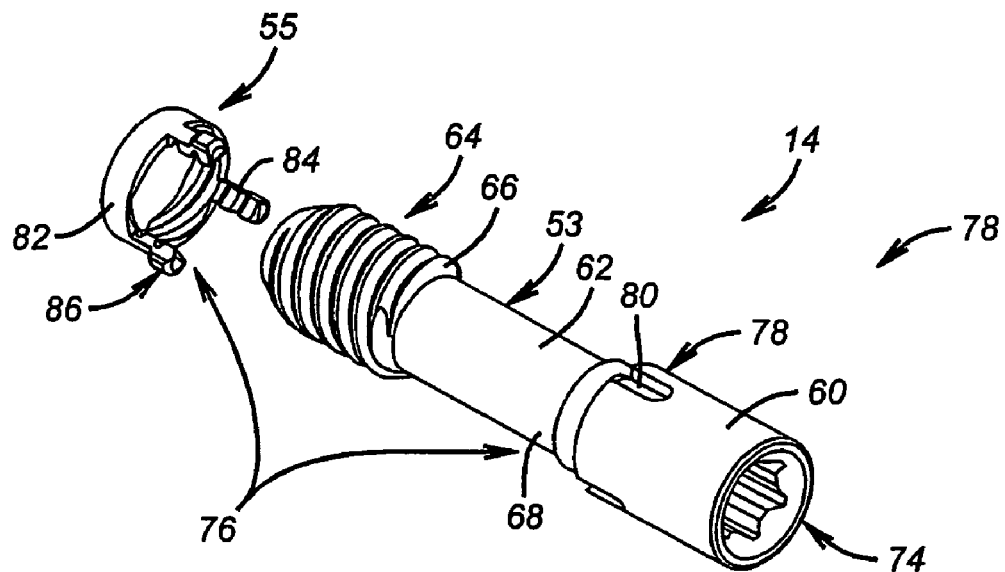
FIG. 4 is an exploded isometric view of the retaining screw of FIG. 3.
Figure 5:
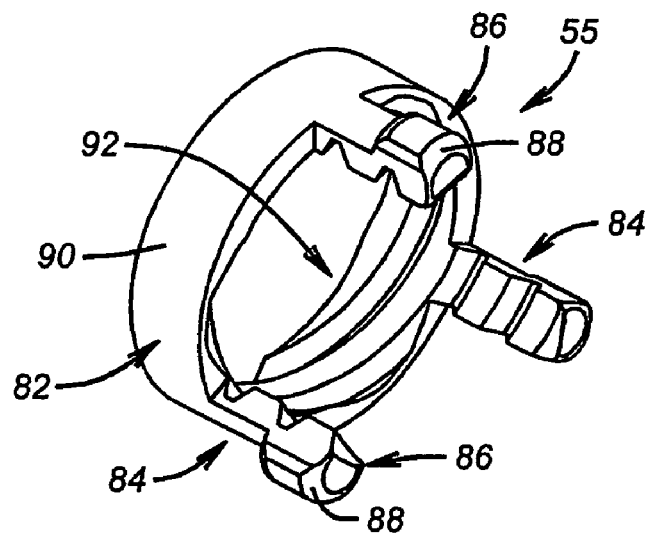
FIG. 5 is an enlarged isometric view of the spring-washer of FIG. 4.
Figure 7:
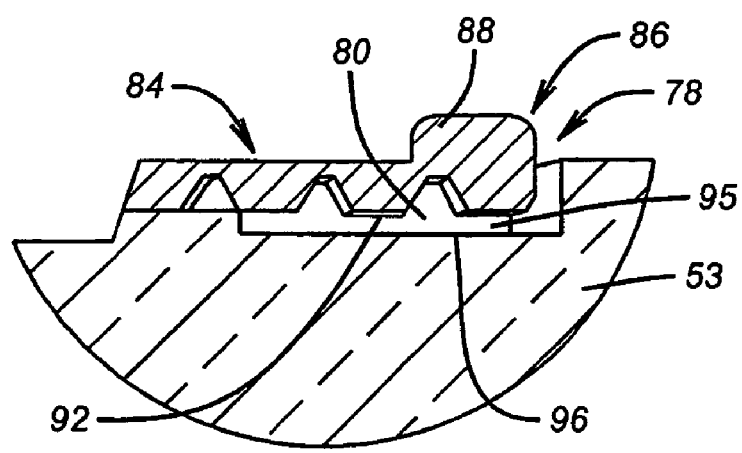
FIG. 7 is an enlarged, side, cross-sectional view along circle 7 of FIG. 6.

As best shown in FIGS. 4 and 5, the spring-washer 55 has a ring-shape or annular body 82. In cross section, this body is generally rectangular. The body 82 has a plurality of legs 84 that extend downwardly and that are equally spaced around the body 82. These legs are resilient or spring-like and have an elongated configuration with a proximal end connected to the body 82 and a distal end with a locking component 86. As best shown in FIG. 7, the locking component 86 is formed as a foot or protrusion 88 that extends outwardly from the distal end of each leg 84.

As shown in FIGS. 4 and 5, the outer surface 90 of the spring-washer 55 is smooth, while the inner surface 92 is threaded. These threads are adapted to threadably engage the threaded portion 64 of the body of the screw. As such, the spring-washer is captured along shank portion 62 between the threaded portion 64 and head 60. The spring-washer could be captured in other ways as well. For example, the outer diameter of the head of the screw could be larger than the inner diameter of the spring-washer.

Figure 6:
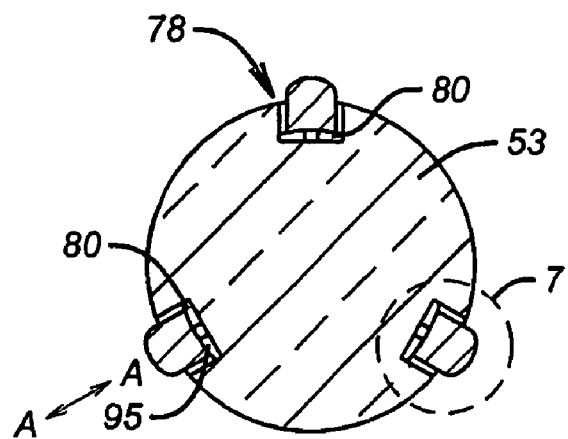
FIG. 6 is a cross-sectional view along lines 6-6 of FIG. 3.

As best shown in FIGS. 6 and 7, the legs 84 of the spring-washer 55 fit inside the channels 80. A small gap or space 95 exists between the inner, threaded surface 92 of each leg 84 and the bottom surface 96 of each channel 80. This gap enables each leg to move in an axial or radial direction (arrows A-A) toward and away from the body 53. The legs, thus, have a resilient or flexible movement while the spring-washer is connected to the body. Further, while the legs 84 are positioned in the housing 78, the foot or protrusion 88 extends partially out of the channels 80.

The housing 78 and the legs 84 may have various configurations known to those skilled in the art. The figures show a generally rectangular configuration, but other shapes which ensure proper bearing, including polygonal shapes (such as square, hemi-spherical, frusto-conical, etc.), are also contemplated.

Preferably, the body of the retaining screw is formed of a biocompatible, corrosive resistant material such as titanium Other materials may work as well, such as steal or other biocompatible, corrosive resistant materials. Preferably, the spring-washer, however, is formed from a second material, different than the material of the body of the abutment. Preferably, this second material is gold. The spring-washer can also be formed a material that is different than the body of the screw. Further yet, the spring-washer can be gold and then coated with titanium.

The gold spring-washer has an advantage in that it provides a reduced coefficient of friction between the contacting surface of the retaining screw and the seating surface of the dental component, such as the abutment. As such, the screw is capable of obtaining a higher preload or clamping force between the dental component and implant.

The spring-washer may be formed from other materials that also reduce the coefficient of friction between contacting surface of the retaining screw and the seating surface of the dental component. For example, the spring-washer can be formed from titanium or other suitable materials and then coated with a diamond-like carbon coating or other coatings or oxidized surfaces, as described in U.S. Pat. No. 6,447,295.

Figure 8:
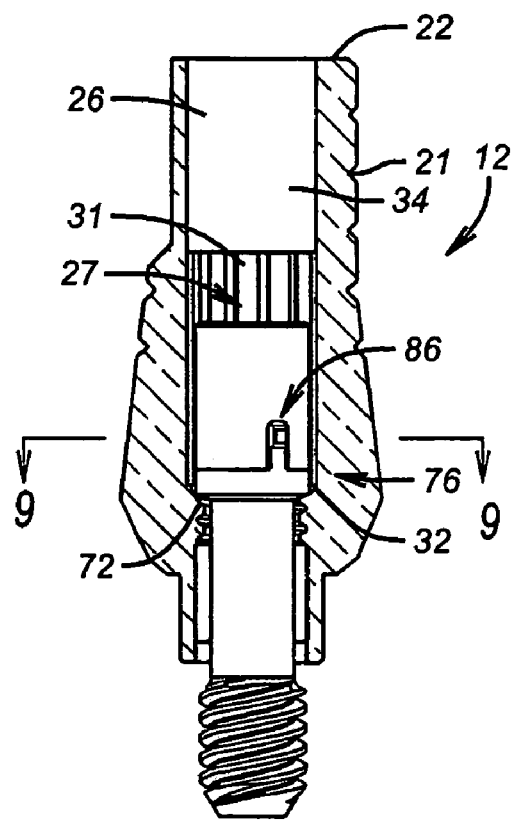
FIG. 8 is a partial cross-sectional view of an abutment and retaining screw according to the invention.
Figure 9:
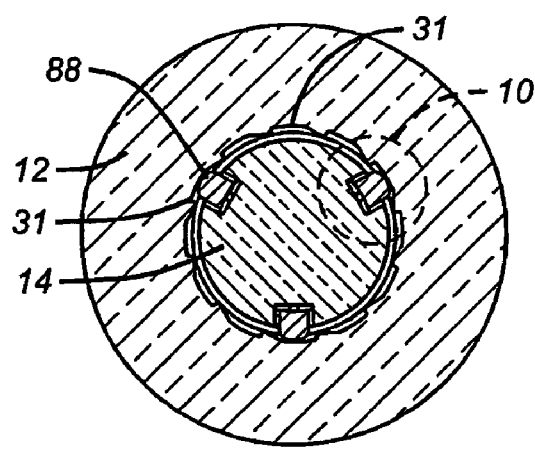
FIG. 9 is an enlarged cross-sectional view along lines 9-9 of FIG. 8.
Figure 10:
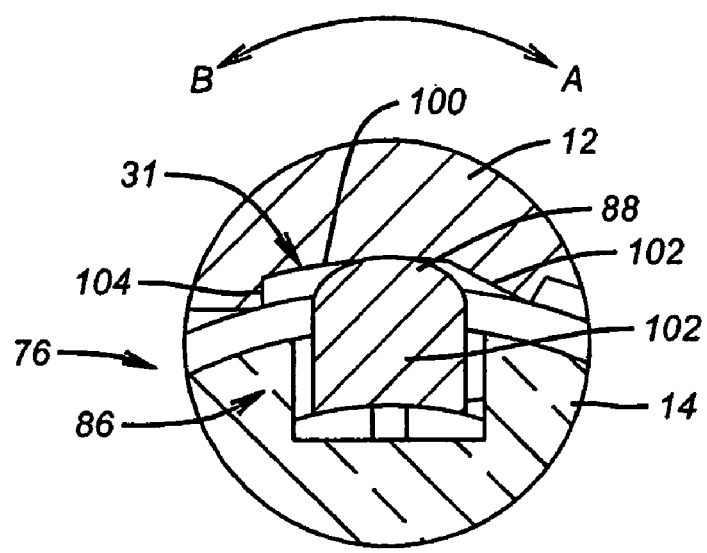
FIG. 10 is an enlarged, cross-sectional view along circle 10 of FIG. 9.

Turning now to FIGS. 8-10, the coupling or engagement between the retaining screw 14 and abutment 12 is shown in detail. The locking mechanism 76 of the retaining screw engages or locks with the locking mechanism 27 of the abutment. Specifically, when the abutting surface 72 of the screw seats or engages with the abutting surface 32 of the abutment, the locking component 86 of the spring-washer 55 is biased into the locking members 31 of the dental component 12. FIG. 10 shows how the foot or protrusion 88 engages or locks with the channels or grooves of the locking member 31. Here, each leg biases the foot in a radial direction so it abuts against a back wall or surface 100 of the locking member 31. The connection or engagement between the locking component 86 and locking members 31, thus, prevents the screw from backing out.

The spring-washer is adapted to threadably engage the exterior threads on the retaining screw. The spring-washer can removeably connect to the body of the screw with any one of various connections, such as a press-fit or snap-fit. Alternatively, the spring-washer can be permanently connected to the body of the retaining screw.

The rotational force or torque required to disengage the locking mechanism 76 of the screw from the locking mechanism 27 of the abutment would be greater than the forces tending to loosen the screw, such as vibrational and occlusal forces like chewing, grinding talking, brushing, etc.

Looking to FIG. 10, the locking member 31 includes the back wall 100, a tapered entry wall or surface 102, and a perpendicular, flat, stop wall or surface 104. When the retaining screw is rotated in a clockwise direction (shown as arrow A) or is being tightened, the feet 88 slide up and along the tapered wall 102. When the screw, however, is rotated in a counterclockwise direction (shown as arrow B) or is being loosened, the feet abut against flat, stop surface 104. This stop surface prevents the locking component 86 from disengaging from the locking mechanism 27 or, more particularly, the locking members 31.

One skilled in the art will appreciate that the locking mechanism 27 of the dental component 12 and the locking mechanism 76 of the retaining screw 14 can have various configurations to provide a locking or anti-rotational engagement. The locking members 31, for example, have a generally rectangular configuration with three surfaces 100, 102, and 104, but other polygonal shapes (such as square, hemi-spherical, frusto-conical etc.) are also contemplated. Further too, the locking component 86 can have various configurations to correspondingly mate with the locking members. The locking component, for example, can be a pin, a button, a cylinder, other geometric configurations, or combinations thereof.

It will be appreciated too that the present invention could incorporate multiple legs and locking components on the spring-washer. Preferably, the spring-washer has three legs, one or more legs can work too.

Figure 11:
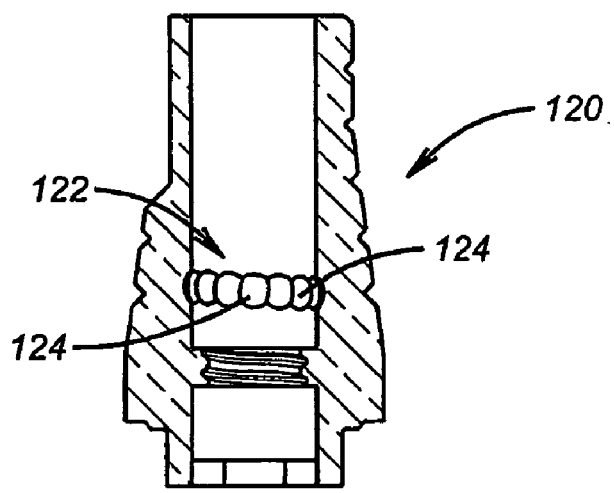
FIG. 11 is a cross-sectional view of another embodiment of an abutment according to the invention.

Further, although FIG. 2 shows the locking members 31 as channels, one skilled in the art will appreciate that the locking mechanism 27 can have various configurations without departing from the scope of the invention. FIG. 11, for example, shows an abutment 120 similar to the abutment 12 in FIG. 2. This abutment 120, however, has a different locking mechanism 122. Here, the locking mechanism 122 includes a plurality of locking members 124 formed as circular indentations or partial spherical indentations. These indentations could have various configurations, such as squares, spheres, rectangles, or other polygonal formations.

Figure 12:
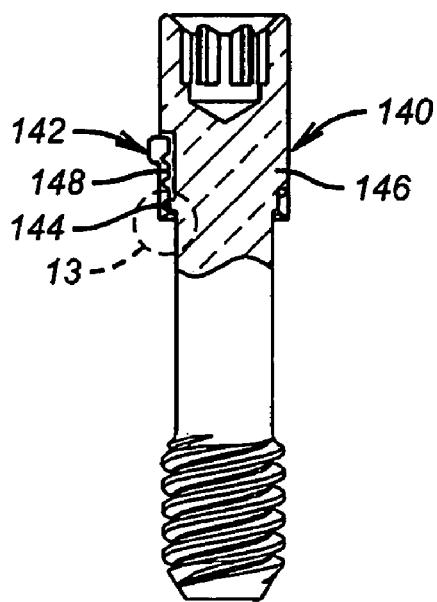
FIG. 12 is a partial cross-sectional view of an alternate embodiment of the retaining screw connected to a spring-washer.
Figure 13:
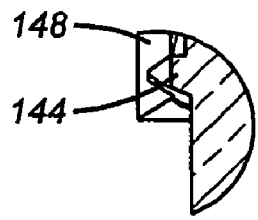
FIG. 13 is an enlarged, side, cross-sectional view along circle 13 of FIG. 12.

Turning now to FIGS. 12 and 13, an alternate embodiment is shown. Here, the retaining screw 140 and spring-washer 142 are generally configured as the retaining screw 14 and spring-washer 55 described in connection with FIGS. 3-5. As one important difference, the retaining screw 140 has a projection or single thread 144 right below the screw head 146. This projection 144 engages with the internal threads 148 of the spring-washer 142 to hold and maintain the spring-washer against the screw head 146.

When a screw is tighten it acts like a clamp that resists the forces that are trying to pry open the joint. When the abutment screw is tightened, it stretches (within elastic limits) and thus generates axial compressive forces. Therefore, the abutment screw acts like a spring. As soon as the screw tightening process is stopped, some of the pre-load is lost.

Figure 14:
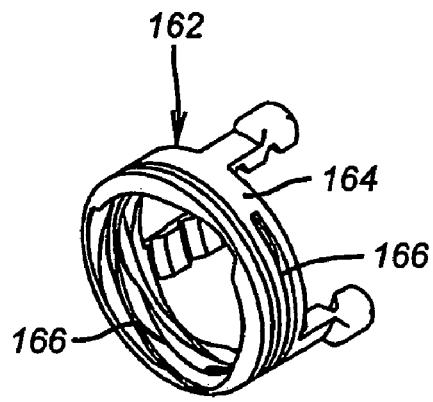
FIG. 14 is an enlarged isometric view of an alternate spring-washer.
Figure 15:
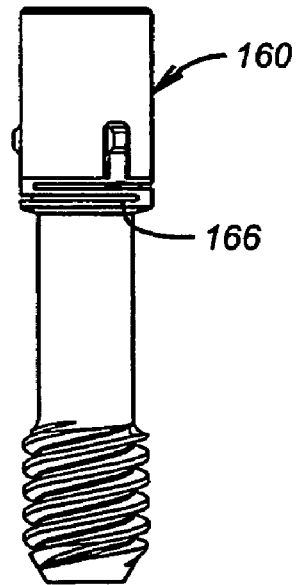
FIG. 15 is a side view of an alternate retaining screw connected to the spring-washer of FIG. 14.

FIGS. 14 and 15 show an alternate embodiment of the spring-washer that is adapted to prevent preload from being lost. Here, the retaining screw 160 and spring-washer 162 are generally configured as the retaining screw 14 and spring-washer 55 described in connection with FIGS. 3-5. As one important difference, the spring-washer 162 is configured to have an axial biasing ability. Specifically, the body 164 of the spring-washer has coils or springs 166 that are moveable in an axial direction. These coils are adapted to bias the body 164 as they are compressed. The coils will become compressed when the retaining screw is seated and tightened against a seating surface.

The present invention can be used with various dental implants and dental accessories, such as abutments, heating components, fixture mounts, copings, analogs, cuffs, or other dental components. Further, as understood by those skilled in the art, the precise configuration and dimensions of the various components of the retaining screw may vary depending upon the size of the implant or dental component. The principles of the present invention can be applied to these various components. Further yet, while preferred embodiments of this invention have been shown and described, modifications thereof can be made by one skilled in the art without departing from the spirit or teaching of this invention.

What is claimed is:

1. A retaining screw and spring washer assembly for fastening a dental component to a dental implant, said assembly comprising:
   a retaining screw further comprising a threaded shank extending from a head, the head comprising a first channel; and
   a washer adjacent to the head, the washer further comprising a first leg extending from an annular body, wherein the first leg is configured for flexible movement within the first channel upon engagement of the first leg with an indentation on an interior bore of the dental component,
   wherein the first leg comprises an extension that extends beyond an outer circumference of the head upon engagement of the first leg with the first channel.

2. A retaining screw and spring washer assembly for fastening a dental component to a dental implant, said assembly comprising:
- a retaining screw further comprising a threaded shank extending from a head, the head comprising a first channel; and
- a washer adjacent to the head, the washer further comprising a first leg extending from an annular body, wherein the first leg is configured for flexible movement within the first channel upon engagement of the first leg with an indentation on an interior bore of the dental component,
- wherein the annular body of said washer comprises a threaded inner surface.

3. A retaining screw and spring washer assembly for fastening a dental component to a dental implant, said assembly comprising:
- a retaining screw further comprising a threaded shank extending from a head, the head comprising a first channel; and
- a washer adjacent to the head, the washer further comprising a first leg extending from an annular body, wherein the first leg is configured for flexible movement within the first channel upon engagement of the first leg with an indentation on an interior bore of the dental component,
- wherein the first leg comprises a threaded inner surface.

4. A dental kit attachable to a coronal end of a dental implant, the kit comprising:
- a dental component further comprising:
  - an elongated body;
  - a bore through the elongated body; and
  - an indentation on the bore;
- a retaining screw disposed through the bore, the retaining screw further comprising:
  - a head having a first channel; and
  - a shank extending from the head, the shank configured for threaded engagement with the coronal end of the dental implant; and
- a washer adjacent to the head, the washer further comprising:
  - an annular body and a first leg extending from the annular body wherein the first leg is configured for flexible movement within the first channel upon engagement of the first leg with the indentation and rotation in a first direction of the retaining screw relative to the dental component.

5. The assembly of claim 4 wherein the indentation has a tapered wall configured to engage the first leg upon rotation in a first direction of the retaining screw relative to the dental component.

6. The assembly of claim 5 wherein the indentation has a flat wall adjacent to the tapered wall wherein the flat wall is configured to abut the first leg upon rotation of said retaining screw in a second direction opposite of the first direction.

7. The assembly of claim 5 wherein:
- said washer comprises a second leg;
- the head of said retaining screw comprises a second channel; and
- the second leg is configured for placement within the second channel upon placement of the first leg within the first channel.

8. The assembly of claim 4 wherein the first leg comprises an extension that extends beyond an outer circumference of the head upon engagement of the first leg with the first channel.

9. The assembly of claim 4 wherein the annular body of said washer comprises a threaded inner surface.

10. The assembly of claim 4 wherein the first leg comprises a threaded inner surface.

11. The assembly of claim 4 wherein the shank of said retaining screw comprises a threaded portion and a non-threaded portion, the non-threaded portion being disposed between the threaded portion and the head of said retaining screw.

12. The assembly of claim 11 wherein the channel is disposed on an end of the head nearest the non-threaded portion of the shank.

13. The assembly of claim 4 wherein the indentation is an elongated groove extending in a longitudinal direction.

* * * * *